(12) United States Patent
Jago et al.

(10) Patent No.: US 11,903,761 B2
(45) Date of Patent: Feb. 20, 2024

(54) ULTRASOUND SYSTEM AND METHOD FOR BREAST TISSUE IMAGING

(71) Applicant: KONINKLIJKE PHILIPS N.V., Eindhoven (NL)

(72) Inventors: James Robertson Jago, Seattle, WA (US); Julia Dmitrieva, Bothell, WA (US); Gary Cheng-How Ng, Redmond, WA (US); Thomas Shu Yin Tang, Richmond Hill, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 34 days.

(21) Appl. No.: 17/863,752

(22) Filed: Jul. 13, 2022

(65) Prior Publication Data

US 2022/0346753 A1 Nov. 3, 2022

Related U.S. Application Data

(62) Division of application No. 16/092,789, filed as application No. PCT/EP2017/059019 on Apr. 13, 2017, now Pat. No. 11,419,577.

(Continued)

(51) Int. Cl.
*A61B 8/14* (2006.01)
*A61B 8/00* (2006.01)
*A61B 8/08* (2006.01)

(52) U.S. Cl.
CPC .......... *A61B 8/4254* (2013.01); *A61B 8/0825* (2013.01); *A61B 8/145* (2013.01);
(Continued)

(58) Field of Classification Search
CPC ..... A61B 8/0825; A61B 8/145; A61B 8/4245; A61B 8/4254; A61B 8/463; A61B 8/465; A61B 8/466; A61B 8/469
See application file for complete search history.

(56) References Cited

U.S. PATENT DOCUMENTS 6,443,896 B1 9/2002 Detmer
6,530,885 B1 3/2003 Entrekin et al.
(Continued)

FOREIGN PATENT DOCUMENTS

CN 102871685 A 1/2013
WO 03101303 A1 11/2003
(Continued)

*Primary Examiner* — Mark D Remaly

(57) ABSTRACT

The present disclosure describes ultrasound imaging systems and methods that may be used to image, for example, breast tissue. An ultrasound imaging system according to one embodiment may include a probe, a sensor attached to the probe and operatively associated with a position tracking system, a processor configured to receive probe position data from the position tracking system. The user interface may be configured to provide instructions for placement of the probe at a plurality of anatomical landmarks of a selected breast of the subject and receive user input to record the spatial location of the probe at each of the plurality of anatomical landmarks. The processor may be configured to determine a scan area based on the spatial location of the probe at each of the plurality of anatomical landmarks and generate a scan pattern for the selected breast. The processor may be further configured to monitor movement of the probe. The user interface may be configured to display, prior to scanning, a visual representation of the scan and automatically update, during scanning, the visual representation of the scan pattern based on movement of the probe.

13 Claims, 10 Drawing Sheets

Related U.S. Application Data

(60) Provisional application No. 62/323,995, filed on Apr. 18, 2016.

(52) U.S. Cl.
CPC ............ *A61B 8/4245* (2013.01); *A61B 8/463* (2013.01); *A61B 8/465* (2013.01); *A61B 8/466* (2013.01); *A61B 8/469* (2013.01)

(56) References Cited

U.S. PATENT DOCUMENTS

| | | |
|---|---|---|
| 7,103,205 B2 | 9/2006 | Wang et al. |
| 7,828,733 B2 | 11/2010 | Zhang et al. |
| 2003/0212327 A1 | 11/2003 | Wang et al. |
| 2012/0113108 A1 | 5/2012 | Dala-Krishna et al. |
| 2014/0058265 A1 | 2/2014 | Wang et al. |
| 2014/0171799 A1 | 6/2014 | Hershey et al. |
| 2014/0343420 A1 | 11/2014 | Zhang |
| 2015/0087979 A1 | 3/2015 | Zhang et al. |
| 2017/0007207 A1 | 1/2017 | Gauthier et al. |

FOREIGN PATENT DOCUMENTS

| | | |
|---|---|---|
| WO | 2011064688 A1 | 6/2011 |
| WO | 2012073164 A1 | 6/2012 |
| WO | 2015087218 A1 | 6/2015 |
| WO | 2015114484 A1 | 8/2015 |
| WO | 2015130037 A1 | 9/2015 |

ULTRASOUND SYSTEM AND METHOD FOR BREAST TISSUE IMAGING

This application is a divisional of U.S. patent application Ser. No. 16/092,789 filing on Oct. 11, 2018, which in turn is the U.S. National Phase application under 35 U.S.C. § 371 of International Application No. PCT/EP2017/059019 filed on Apr. 13, 2017, which claims the benefit of Provisional Application Ser. No. 62/323,995, filed Apr. 18, 2016. These applications are hereby incorporated by reference herein.

BACKGROUND

The present disclosure relates generally to medical imaging systems such as ultrasound imaging systems. An ultrasound imaging system, which may be a cart-based ultrasound imaging system, typically includes a user interface which operates in conjunction with a probe and a display to acquire and display images from a subject, such as a patient. Medical imaging systems may be used for screening and diagnostics purposes such as to identify the presence of and/or quantify parameters associated with a tumor in a tissue of the subject. Accurate and early identification and assessment of a tumor may facilitate more effective treatment response. For example, in the case of breast cancer, ultrasound imaging has more recently found use in screening and diagnosis of breast cancer.

Automated systems for breast screening have been developed. Such systems utilize an actuated gantry to automatically or semi-automatically control the movement of the ultrasound probe with respect to the patient's breast. Although some automated ultrasound breast screening systems now exist, freehand ultrasound breast screening is still a clinically accepted and often preferred breast screening method. In freehand ultrasound breast screening, an operator (e.g., a sonographer or a clinician) controls the movement of the probe. In freehand breast screenings, the operator controls not only the movement of the probe but also the applied pressure, both of which may affect the quality of the scan. The quality of freehand ultrasound breast screening/imaging, as with other ultrasound imaging operations may be highly dependent on the operator's skill and experience. Also, due to a typically smaller size of the probe relative to the area of interest (e.g., full breast tissue) and smaller field of view as compared to other imaging modalities (e.g., MM, CT, x-ray), a single ultrasound image may not provide a full image of the breast. Multiple sweeps with an ultrasound probe are typically used to acquire image data of the full breast, for example during a screening procedure. The examples described herein may provide solutions to one or more challenges in the field of freehand ultrasound breast screening.

SUMMARY

An ultrasound imaging system according to one embodiment, may include a probe, a sensor attached to the probe and operatively associated with a position tracking system, a processor configured to receive probe position data from the position tracking system and determine a spatial location of the probe with respect to a subject, and a user interface. The user interface may be configured to provide instructions for placement of the probe at a plurality of anatomical landmarks of a selected breast of the subject and receive user input to record the spatial location of the probe at each of the plurality of anatomical landmarks. The processor may be further configured to determine a scan area based on the spatial location of the probe at each of the plurality of anatomical landmarks and generate a scan pattern for the selected breast. The processor may be configured to monitor movement of the probe. The user interface may be configured to display a visual representation of the scan pattern prior to scanning of the selected breast, and automatically update the visual representation of the scan pattern based on movement of the probe during scanning of the selected breast.

Aspects of the present disclosure, such as certain elements of the user interfaces described herein and/or functions performed by a processor of the ultrasound system, may be embodied in computer-readable media comprising processor-executable instructions. For example, processor-executable instructions for providing one or more graphical user interfaces or elements thereof may be incorporated into a software package, for example for execution on an analysis workstation. Aspects of the present disclosure may facilitate offline image analysis as described further below, however it will be understood that the principles described herein may be equally applied to online image analysis (e.g., analysis performed during or shortly after image acquisition). In accordance with one embodiment, a non-transitory computer-readable medium comprising processor-executable instructions for displaying ultrasound images may include instructions to display a first image frame from a first plurality of stored image files, wherein the image file contains first position information corresponding to a probe position during acquisition of the first image frame, receive, via a user interface, a request for an orthogonal view, compare the first position information with position information for a second plurality of stored image files to identify one or more images frames in the second plurality associated with position information closest to the first position information, and display a representation of each of the one or more image frames as candidate orthogonal views.

DETAILED DESCRIPTION

Figure 1:
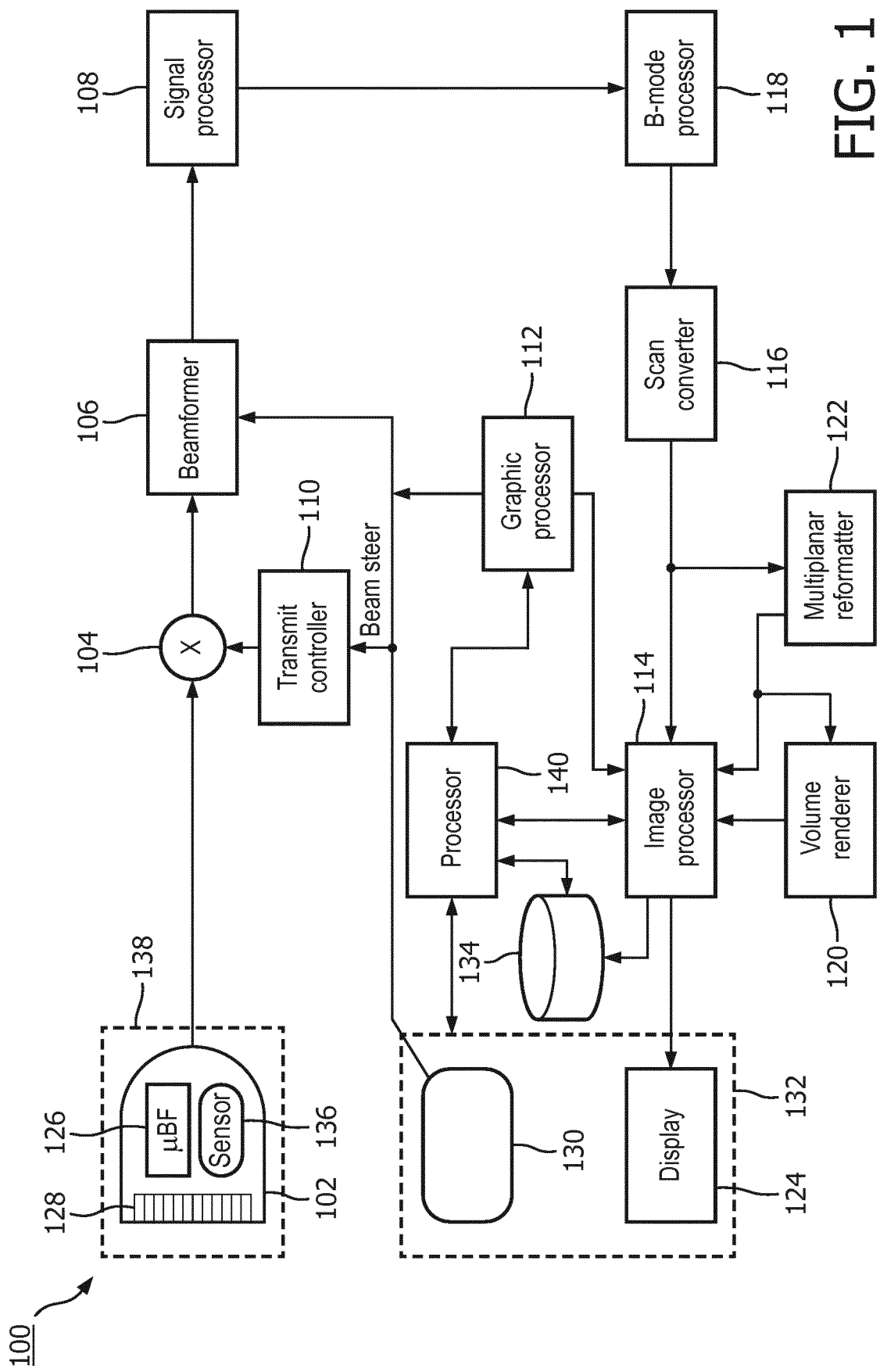
FIG. 1 shows a block diagram of an ultrasound imaging system in accordance with one embodiment.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The use of ultrasound for breast screening, especially in women with mammographically dense breasts, is a rapidly developing trend throughout the world. Breast density is considered one of the strongest predictors of the failure of mammography to detect cancer and is also a well-established predictor of breast cancer risk. During breast ultrasound screening, an operator, who may or may not be skilled in interpreting ultrasound images, acquires ultrasound images covering all of the breast tissue. The acquisition of image data may be performed freehand or with some level of automation such as by automated control of the movement of the probe. The image data may be reviewed online (e.g., on a display of the ultrasound imaging system and/or during the image data acquisition process) or offline (e.g., on a processing workstation following the image data acquisition process). In some cases, the reading and interpretation of these images may be performed very efficiently off-line by a radiologist. In conventional diagnostic ultrasound, where a suspicious lesion is being characterized, it is typical clinical practice to visualize, record, and measure the lesion in two orthogonal planes in order to gain more confidence in identifying suspicious or benign findings. The ability to visualize and measure a lesion in two orthogonal views may thus also be important for breast screening, e.g., to help determine if the lesion is suspicious enough to warrant a recall for a diagnostic exam and/or to document the 3-dimensional size of the lesion. Certain difficulties in the acquisition and review of breast tissue image data may be addressed by the examples herein, for example by providing a user interface which may assist a user during freehand breast screening. Examples herein may, additionally or alternatively, enable more efficient review of acquired image data.

Referring to FIG. 1, an ultrasound imaging system 100 constructed in accordance with the principles of the present invention is shown in block diagram form. The ultrasound imaging system 100 may be used to implement, at least in part, any of the ultrasound imaging systems described herein. FIG. 1 shows an ultrasound imaging system 100, which includes ultrasound probe 102, transducer array 128, microbeamformer 126, transmit/receive (T/R) switch 104, beamformer 106, transmit controller 110, signal processor 108, B-mode processor 118, scan converter 116, multiplanar reformatter 122, volume renderer 120, image processor 114, graphics processor 112, user interface 132, input device 130, and output device 124. The components shown in FIG. 1 are merely illustrative, and other variations, including eliminating components, combining components, rearranging components, and substituting components are all contemplated.

In the ultrasound imaging system 100 in FIG. 1, the ultrasound probe 102 includes a transducer array 128 for transmitting ultrasonic waves and receiving echo information. A variety of transducer arrays are well known in the art, e.g., linear arrays, convex arrays or phased arrays. The transducer array 128 for example, can include a two dimensional array of transducer elements capable of scanning in both elevation and azimuth dimensions for 2D and/or 3D imaging. The transducer array 128 is coupled to a microbeamformer 126, typically located in the ultrasound probe 102, which controls transmission and reception of signals by the transducer elements in the array. In this example, the microbeamformer 126 is coupled, such as by a probe cable or wirelessly, to a transmit/receive T/R switch 104, which switches between transmission and reception. The T/R switch 104 may thus protect the beamformer 106 from high energy transmit signals. In some embodiments, the T/R switch 104 and other elements of the system can be included in the transducer probe rather than in a separate ultrasound system base.

The transmission of ultrasonic beams from the transducer array 128 under control of the microbeamformer 126 is directed by the transmit controller 110 coupled to the T/R switch 104 and the beamformer 106. The transmit controller 110 receives input from the user's operation of an input device 130 of user interface 132. The user interface 132 may be implemented using one or more input, such as control panels which may include soft and/or hard controls, and output devices, such as one or more displays, as described further below. One of the functions controlled by the transmit controller 110 is the direction in which beams are steered. Beams may be steered straight ahead from (orthogonal to) the transducer array, or at different angles for a wider field of view. The partially beamformed signals produced by the microbeamformer 126 are coupled to a beamformer 106 where partially beamformed signals from individual patches of transducer elements are combined into a fully beamformed signal.

The beamformed signals may be coupled to a signal processor 108. The signal processor 108 can process the received echo signals in various ways, such as bandpass filtering, decimation, I and Q component separation, and harmonic signal separation. The signal processor 108 may also perform additional signal enhancement such as speckle reduction, signal compounding, and noise elimination. The processed signals may be coupled to a B-mode processor 118, which can employ amplitude detection for the imaging of structures in the body. The signals produced by the B-mode processor may be coupled to a scan converter 30 and a multiplanar reformatter 122. The scan converter 116 arranges the echo signals in the spatial relationship from which they were received in a desired image format. For instance, the scan converter 116 may arrange the echo signal into a two dimensional (2D) sector-shaped format, or a pyramidal three dimensional (3D) image. The multiplanar reformatter 122 can convert echoes which are received from points in a common plane in a volumetric region of the body into an ultrasonic image of that plane, as described in U.S. Pat. No. 6,443,896 (Detmer). A volume renderer 120 converts the echo signals of a 3D data set into a projected 3D image as viewed from a given reference point, e.g., as described in U.S. Pat. No. 6,530,885 (Entrekin et al.) The 2D or 3D images may be coupled from the scan converter 116, multiplanar reformatter 122, and volume renderer 120 to an image processor 114 for further enhancement, buffering and temporary storage for display on an output device 124. The output device 124 may include a display device implemented using a variety of known display technologies, such as LCD, LED, OLED, or plasma display technology.

The graphics processor 112 can generate graphic overlays for display with the ultrasound images. These graphic overlays can contain, e.g., standard identifying information such as patient name, date and time of the image, imaging parameters, and the like. The graphics processor may receive input, such as a typed patient name, from the input device 130. The input device 130 may include one or more mechanical controls, such as buttons, dials, a trackball, a physical keyboard, and others, which may also be referred to herein as hard controls. Alternatively or additionally, the input device 130 may include one or more soft controls, such as buttons, menus, soft keyboard, and other user interface control elements implemented for example using touch-sensitive technology (e.g., resistive, capacitive, or optical touch screens). To that end, the ultrasound imaging system 100 may include a user interface processor (i.e., processor 140), which may control operations of the user interface such as functions associated with soft controls. One or more of the user controls may be co-located on a control panel. For example one or more of the mechanical controls may be provided on a console and/or one or more soft controls may be co-located on a touch screen, which may be attached to or integral with the console.

The ultrasound images and associated graphics overlays may be stored in memory 134, for example for off-line analysis. In addition, the memory 134 may store processor-executable instructions including instructions for performing functions associated with the user interface 132. The user interface 132 can also be coupled to the multiplanar reformatter 122 for selection and control of a display of multiple multiplanar reformatted (MPR) images. In some examples, functionality of two or more of the processing components (e.g., beamformer 106, signal processor 108, B-mode processor 118, scan converter 116, multiplanar reformatter 122, volume renderer 120, image processor 114, graphics processor 112, processor 140, etc.) may be combined into a single processing unit.

In accordance with the examples herein, a sensor 136 may be attached to the ultrasound probe 102 and operatively associated with a position tracking system 138 such that the position of the probe in space can be tracked and/or recorded. A processor of the ultrasound imaging system 100 (e.g., processor 140) may be configured to receive probe position data from the position tracking system 138 to determine the spatial location of the probe with respect to a subject (e.g., a patient). To that end, the ultrasound imaging system 100 may be configured to register the ultrasound probe 102 with respect to the subject, as will be described further below. In this manner, the processor 140 may be able to monitor movement of the probe in space and/or with relation to the subject such as by detecting changes in the spatial location of the probe using the position data from the position tracking system 138. The processor 140 may be further configured to associate the position of the probe during acquisition of a particular image frame with that frame such that ultrasound images may be stored with the associated probe position information for ease of subsequent retrieval and analysis.

In some examples, an ultrasound imaging system may include a probe, a sensor attached to the probe and operatively associated with a position tracking system, a processor configured to receive probe position data from the position tracking system and determine a spatial location of the probe with respect to a subject, and a user interface. The user interface may be configured to guide the user through a registration process, such as by guiding the user through placing the probe at a plurality of anatomical landmarks, the user interface receiving user input to record the spatial location of the probe at those anatomical landmarks. In some examples, the user interface may provide instructions for placement of the probe at a plurality of anatomical landmarks of a selected breast of the subject and receive user input to record the spatial location of the probe at each of the plurality of anatomical landmarks. An example method that could be used for registration of the patient's anatomy to the position sensing system is described although other methods that the specific example described may also be used. Registration may be used to provide input of the patient's physical position in relation to any position sensing system, and to provide anatomical inputs like the location of the nipple and the boundaries and size of the breast. The processor may be configured to monitor movement of the probe based on detected changes in the spatial location of the probe. The user interface may be configured to display, prior to scanning the selected breast, a visual representation of the scan pattern, and automatically update, during scanning of the selected breast, the visual representation of the scan pattern based on movement of the probe. The user interface may also be configured to track and highlight the areas for which the system has recorded any image data (e.g., loops or still frames) to indicate to the user which regions have been scanned.

Figure 2:
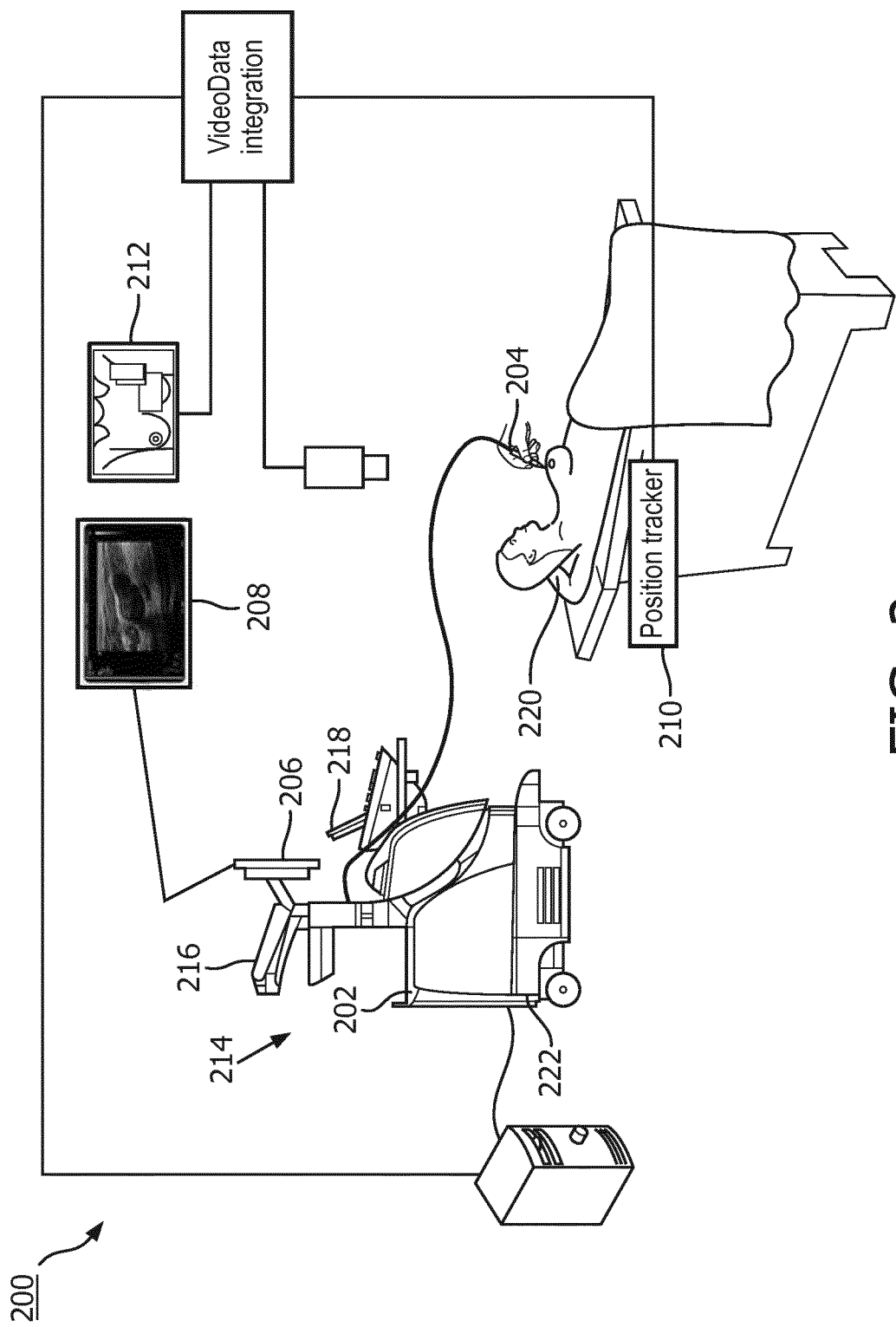
FIG. 2 shows an illustration of an ultrasound imaging system, which may be used to scan breast tissue for example when performing a freehand breast screening.

FIG. 2 shows an illustration of an ultrasound imaging system which may be used to scan breast tissue, e.g., when performing a freehand breast screening. FIG. 2 shows an ultrasound imaging system 200, ultrasound imaging device 202, probe 204, display 206, position tracking system 210, and patient 220. The components shown in FIG. 2 are merely illustrative and other variations, including eliminating components, combining components, rearranging components, and substituting components are all contemplated.

The ultrasound imaging system 200 may include one or more of the components of the ultrasound imaging system 100 in FIG. 1. The ultrasound imaging system 200 may include an ultrasound imaging device 202, which may be a cart-based ultrasound imaging device, a handheld imaging device, or other portable imaging device. For example, one or more of the processing components of the ultrasound imaging device 202 (e.g., beamformer, signal processor, B-mode processor, scan converter, multiplanar reformatter, volume renderer, image processor, graphics processor, and/or other processors which may control various operations of the ultrasound imaging device) may be provided in a base 222, which may be a mobile base. The ultrasound imaging device 202 may be connected to a probe 204 via wired (e.g., cable) or wireless (e.g., Wi-Fi) connection. The probe 204 may be used scan breast tissue of a subject (e.g., patient 220). The probe 204 may be configured for freehand operation. By freehand, it is generally meant that the probe is handled (e.g., moved) by an operator (e.g., ultrasound technician) during scanning rather than by a machine-controlled actuator. Operation of the probe 204 may be controlled, in part, via the user interface 214. The user interface 214 may include input components, such as mechanical and soft controls, and output components, such as visual, audible and tactile feedback devices. One or more components of the user interface 214 may be implemented using graphical user interface elements. For example, the ultrasound imaging device 202 may include one or more displays (e.g., display 206), and one or more user interface elements (e.g., graphical user interface elements) of the user interface 214 may be provided on the display 206. The ultrasound imaging device 202 may include a touch screen 218, which may be operable to display user controls (e.g., GUI controls, which may also be referred to as soft controls). In some examples, the touch screen 218 may be configured to also display acquired images. In other words, acquired images (e.g., live image 208) may also be displayed on the display 206, the touch screen 218, or both. The display 206 may be attached to the base 222 via an articulating arm 216 for re-positioning the display 206 such as to allow a displayed image to be viewable by others (e.g., the patient, another ultrasound operator, or a clinician).

The ultrasound imaging system 200 may be configured to display a live image 208 (e.g., a live image of an area of interest), for example on display 206. The ultrasound imaging system 200 may be operatively associated with a position tracking system 210. The position tracking system 210 may be an electromagnetic (EM) tracking system. An EM tracking system typically includes an EM field generator and a sensor. The sensor may be attached to the probe 204 (e.g., embedded in or externally to the housing of the probe 204). In some examples, a tabletop EM field generator may be used. The EM field generator may be movable with respect to a support surface supporting the subject (e.g., an examination table) and thus with respect to the patient. This may enable re-positioning of the EM field generator such that the EM field encompasses the organ or tissue to be scanned (e.g., left breast, right breast). In some examples, the EM field generator may be fixed with respect to the support surface. The position tracking system 210 may thus provide estimates of the position of the probe 204, which may enable the ultrasound imaging system 200 to provide guidance to the operator during freehand scanning, as will be further described. In some examples, a different type of position tracking system may be used, such as an optical tracking system.

In some examples, the ultrasound imaging system 200 may be further configured to provide feedback to the operator (e.g., sonographer), for example via a feedback display element 212, of a scanned area. The feedback display element 212 may dynamically update as ultrasound image data is being acquired to provide visual indication of the area that has already been scanned and the area that remains to be scanned. In some examples, the feedback display element 212 may be provided on a display that is viewable by the patient such that the patient may also visualize the progress of the scan, which may result in a better patient experience.

Figure 3:
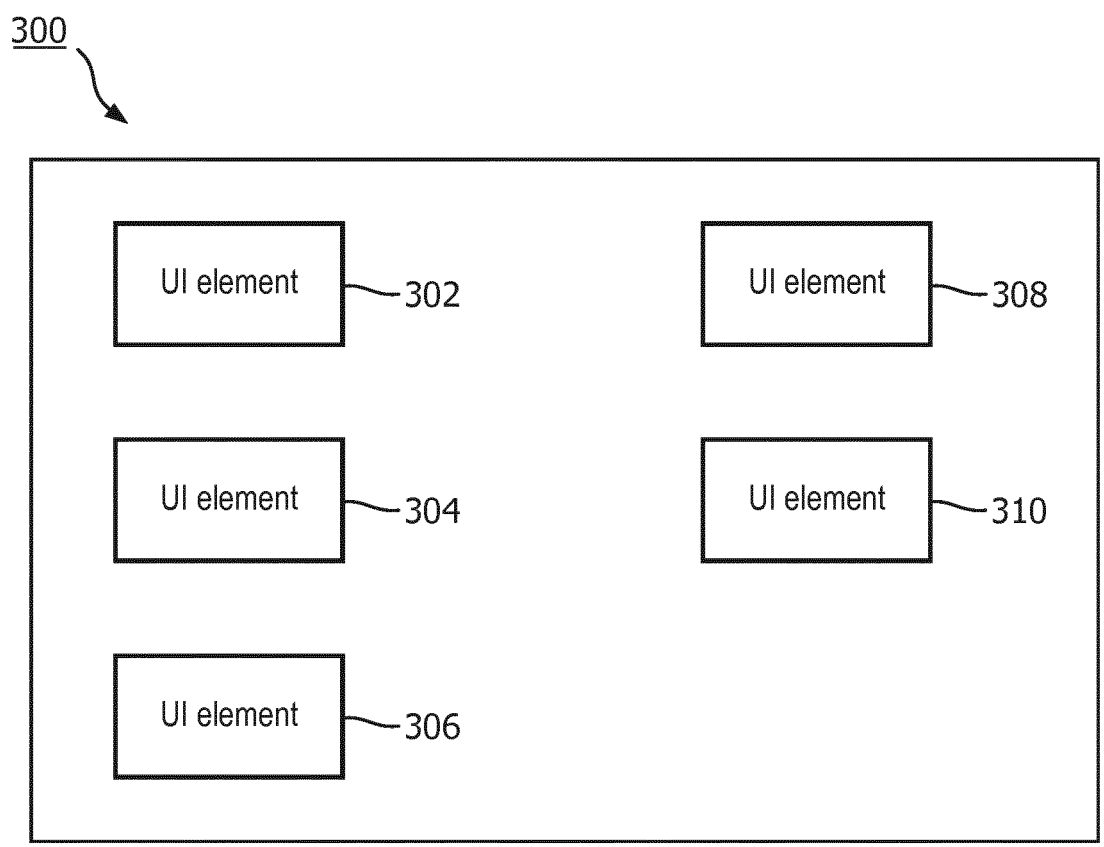
FIG. 3 shows a block diagram of a user interface in accordance with one embodiment.

FIG. 3 shows a block diagram of a user interface 300 according to one embodiment. The components shown in FIG. 3 are merely illustrative and other variations, including eliminating components, combining components, rearranging components, and substituting components are all contemplated. The user interface 300 or components thereof may be used to implements aspects of user interfaces described herein. FIG. 3 shows a user interface 300, and user interface (UI) elements 302, 304, 306, 308, and 310, one or more of which may be GUI elements which are provided on a display of the ultrasound system. One or more of the UI elements may implement user controls (e.g., GUI controls or soft controls) and may be provided on a touch-sensitive display (e.g., touch screen 218). It will be appreciated that the elements 302, 304, 306, 308, and 310 in the illustrated example need not be provided concurrently on a same display screen but may be provided sequentially or different times during use of the ultrasound system. For example one or more of the elements 302, 304, 306, 308, and 310 may be provided initially on a first display screen and other ones of the elements 302, 304, 306, 308, and 310 may be provided on the same display device but at a later time and/or on a different display device concurrently or at a different time.

A user interface in accordance with the examples herein may be configured to enable the user to register the probe. For example, the user interface 300 may include a first user interface element 302 which may provide instructions for placement of the probe at a plurality of anatomical landmarks of a selected breast of the subject, also referred to as probe spatial registration instructions. The probe spatial registration instructions may guide the user (e.g., ultrasound operator) through a probe registration process which enables the ultrasound imaging system to spatially register the probe with respect to a subject (e.g., patient 220). During the probe registration process, the user is instructed to place the probe at predetermined anatomical landmarks, in this case breast landmarks, and the spatial location of the probe at each of the breast landmarks is associated with the respective landmark to generate probe registration position data. The breast landmarks may be located at boundaries of the breast, thus enabling a processor of the ultrasound system to determine the size and laterality for each breast (e.g., left breast, right breast). In some examples, the probe registration position data may be used to determine a scan area based on the size and/or laterality of the selected breast. The scan area may be bounded by lines passing through the points marked as corresponding to the anatomical landmarks. As an aide to help the user optimally scan the breast tissue, the processor may generate a recommended scan pattern for the selected breast side. In some examples, the scan pattern may be a standard, non-customized graphic which provides general guidance for a recommended sweep technique. In some examples, the scan pattern may be based, in part, on the scan area and thereby customized to the specific subject to be scanned. For example, the scan pattern may be configured to guide the user to move the probe along a path that's selected to enable the probe's footprint to traverse the full surface area of the scan area.

In accordance with some examples, the user interface may be configured to display a visual representation of the scan pattern, e.g., to guide the user during image data acquisition. For example, user interface 300 may include a second user interface element 304, which may include the visual representation of the scan pattern. The scan pattern may include a one or more continuous or discontinuous scan path lines. The operator may be instructed to move the probe along the surface of the breast following the scan path lines in order to obtain sufficient data to image the full area of interest (e.g., the full left breast or full right breast). In some examples, a scan area that is smaller than the full breast may be defined, such as for a focused study of a region of interest that includes a lesion.

The ultrasound system may generate a scan pattern based on one or more parameters, some of which may be user configurable. For example, as previously described, the scan pattern may be based on the scan area and the footprint of the probe. The footprint of the probe may depend on the type of probe used, which may be specified by the user (e.g., via user interface 300) or automatically detected by the ultrasound system. The processor may be configured to generate a pattern that includes one or more scan path lines along the surface of the breast such that if the operator sweeps the probe along the scan path lines, the probe's footprint is estimated to cover the full scan area. It will be understood that in some embodiments, the user interface may not include one or more of the UI element, for example the user interface may not include UI element 304.

In some examples, the scan pattern may also be based on a user-selected scan pattern type (e.g., raster type, radial/anti-radial type, etc.) as described further below. The scan pattern may be based further in part on desired view plane overlap, which may be pre-programmed and/or user-configurable. The view plane overlap may also depend on the type of probe (e.g., linear, curvilinear), which as previously described may be user-specified or automatically detected by the system. In this regards, the user interface 300 may include a third user interface element 306, which may enable the user to specify user-configurable parameters for generating the scan pattern. The third user interface element 306 may include one or more icons, menus, or text input fields, which may enable the user to select or otherwise specify the values for scan parameters. For example, the third user interface element 306 may be configured for receiving one or more user inputs, such as scan pattern type selection, probe type selection, desired view plane overlap selection, and others. In some examples, the user interface may enable the user to select a scan direction (e.g., side-to-side, up/down) and the system may store recorded images within distinct sets based on the selected scan direction. That is, the system may store one group of images into a first set when a first scan direction is selected and the system may store another group of images into a second set (e.g., an orthogonal set) when a second scan direction is selected. The term orthogonal as used herein is not meant to be limited to perfectly orthogonal view but is meant to include images that are nearly or approximately orthogonal. That is, in some examples an image that is described as orthogonal may display a view plane that is approximately orthogonal (e.g., up to plus or minus 15 degrees). In some examples, the images in one set, e.g., as obtained from sweeps in one direction, may be angled although not necessarily orthogonal to images in another set, e.g., as obtained from sweeps in another direction.

The user interface 300 may be configured to automatically update the visual representation of the scan pattern based on movement of the probe. For example, the position tracking information may enable the processor to determine a deviation from the expected path (e.g., as defined by the scan pattern) and recalculate the path to reduce the risk of gaps in the acquired image data. In the case of excess deviation, the processor may generate a new scan pattern and the visual representation of the scan pattern may be updated with the new scan pattern.

The user interface 300 may include a fourth user interface element 308, which may be configured to provide feedback of a scanned area. In some examples, the fourth user interface element 308 may be configured to display an illustration of a breast (e.g., a breast graphic) overlaid with an area marker corresponding to the estimated area of breast that has been scanned. The fourth user interface element 308 may be dynamic in that it may be automatically updated as the operator scans the breast. The user interface 300 may thereby improve the ease, efficiency, and quality of freehand breast screening by providing real-time feedback to the operator of the area that has already been scanned.

The user interface 300 may include a fifth user interface element 310, which may be configured to display an acquired image, such as a live ultrasound image. In some examples, the fifth user interface element 310 may be configured to display a cineloop in real time as image data is being acquired.

Figure 4:
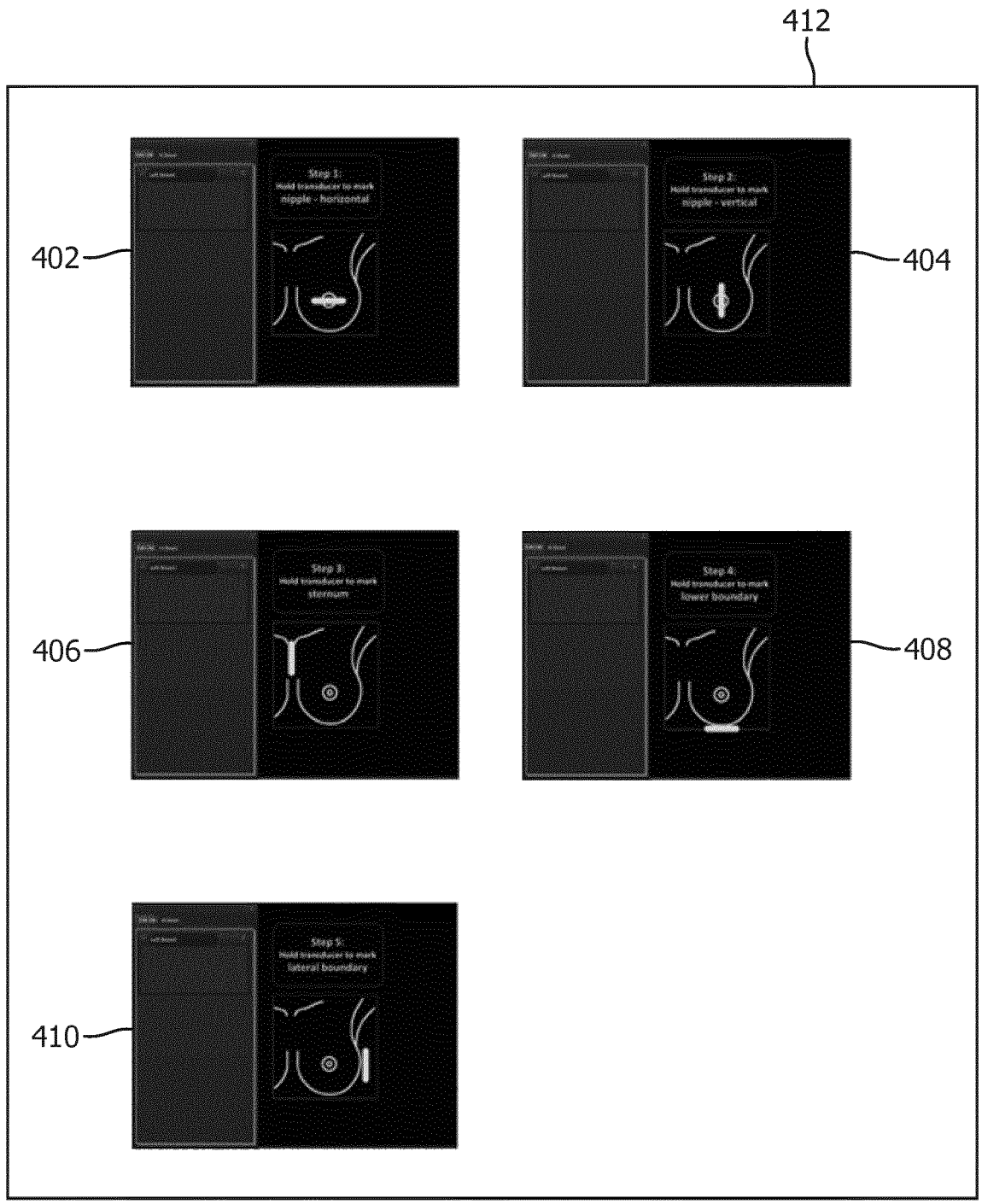
FIG. 4 shows user interface elements in accordance with some examples of the present disclosure.

FIG. 4 illustrates a user interface 412 in accordance with further examples of the present disclosure. FIG. 4 shows first registration UI element 402, second registration UI element 404, third registration UI element 406, fourth registration UI element 408, and fifth registration UI element 410. One or more of the user elements of user interface 412 may be used to implement one or more UI elements of user interfaces described herein. For example, one or more of the UI elements 402, 404, 406, 408, and 410 may be used to implement the first user interface element 302. The components shown in FIG. 4 are merely illustrative and other variations, including eliminating components, combining components, rearranging components, and substituting components are all contemplated.

As described, the user interface of ultrasound systems in accordance with the present disclosure may be configured to provide probe spatial registration instructions. To that end, user interface 412 may include a plurality of registration UI elements, such as first registration UI element 402, second registration UI element 404, third registration UI element 406, fourth registration UI element 408, and fifth registration UI element 410. Each of the registration UI elements may be configured to provide instructions to an operator for placement of the probe relative to the subject. The registration UI elements may be graphical user interface elements (e.g., icons) and the instructions may be visual, such as through a display of a text or a visual representation of an action to be taken by the operator. For example, a visual representation of an action to be taken may be provided in the form of a graphic of the tissue or organ, in this case the selected left or right breast, overlaid with the location where the probe is to be positioned with respect to the breast. In the case of breast scanning, in some examples, the user may be instructed to position the probe at the nipple, lower and outer boundaries of the breast, and the sternum. Other landmarks may be used. In yet further examples, the registration UI elements may be implemented differently, for example another kind of visual instruction, using audible instructions, tactile instructions or combinations thereof.

In the illustrated example, the probe spatial registration instructions are provided in the form of GUI elements. In this example, each of the registration UI elements is implemented in the form of an icon which includes a breast graphic overlaid with a probe placement marker. In this regard, the illustrated GUI elements may interchangeably be referred to as registration icons 402, 404, 406, 408, and 410. The registration icons may be displayed (e.g., on a display 206) in sequence, one after the completion (e.g., marking of the breast landmark) of a previous icon. In some examples, two or more of the icons may be provided concurrently on a display and the active icon may be indicated such as by illuminating a portion (e.g., a border) of the icon, while the icon remains active. As each of the icons is displayed or otherwise activated, the ultrasound system may record the spatial location of the probe at the corresponding landmark, such as responsive to user input. In other words, the user interface 412 may display an icon and record the probe's spatial location responsive to confirmatory user input (e.g., responsive to the pressing of a hard or soft control) that the probe has been placed at the specified location. The system may associate the probe's spatial location with the landmark illustrated in the displayed icon, and proceed to the next landmark. The probe's spatial locations at each landmark location may collectively be referred to as probe spatial registration information.

As illustrated, the first registration icon 402 may include a breast graphic overlaid with a first probe placement marker, which is arranged horizontally centered on the nipple. The second registration icon 404 may include a similar breast graphic overlaid with a second probe placement marker, which is arranged vertically centered on the nipple. Based on position data recorded responsive to the first and second registration UI elements, the system may determine the center of the nipple. A third registration icon 406 may include a breast graphic overlaid with a third probe placement marker, arranged vertically at the sternum. The fourth and fifth icons 408 and 410, respectively, may each include a similar breast graphic overlaid with probe placement markers at a boundary of the selected breast (e.g., below the breast and on the outside of the selected breast, respectively).

As described, the registration UI elements may be provided in sequence and the system may pause until user input is received marking the position. The user may mark the position by operating a user control (e.g., pressing a soft key, a button or other type of hard or soft control) after the probe has been placed at the instructed landmark. Alternatively, the system may be configured to detect lack of motion of the probe for a period of time (e.g., 3 seconds, 4 seconds or more) and may automatically mark the position. The user interface 412 may provide feedback to confirm that the position has been marked. The feedback may be visual such as by illuminating a portion of the icon, audible such as by generating a beep or other sound, or tactile such as by vibrating a portion of the touch screen or probe. In some examples, displaying the next UI element in the sequence may serve as the feedback that the previous position has been properly marked.

In other examples, the user interface 412 may be configured to display two or more registration UI elements on the same screen, and the user may select (e.g., click on or hover over) a registration UI element to activate it, place the probe and mark the position, then proceed through each of the registration UI elements in similar manner. Each of the registration UI elements may also provide an indication of the breast that is being registered against (e.g., the left breast or the right breast), for example in the form of a label and/or by virtue of the graphic of the icon corresponding to the selected breast side. In the illustrated examples, a left breast is selected for registration and the indication is provided both using a label and via the graphic. In other examples, different combinations may be used.

Following registration of the probe, the processor (e.g., processor 140) may determine a scan area and generate a scan pattern for the selected breast side. As described, the user interface (e.g., user interface 132) may be configured to display a visual representation of the scan pattern. The visual representation of the scan pattern may be implemented in the form of an icon that includes a breast graphic overlaid with the scan pattern (interchangeably referred to herein as scan pattern icon). Similar to the registration icons, the breast graphic in the scan pattern icons may correspond to the selected breast side. One or more scan pattern icons may be displayed initially (e.g., prior to scanning) to enable the user to select a scan pattern type, or in other examples the user may specify the scan pattern type via textual input (e.g., by typing "raster" or "radial," in a text input box of the user interface).

Figure 5:
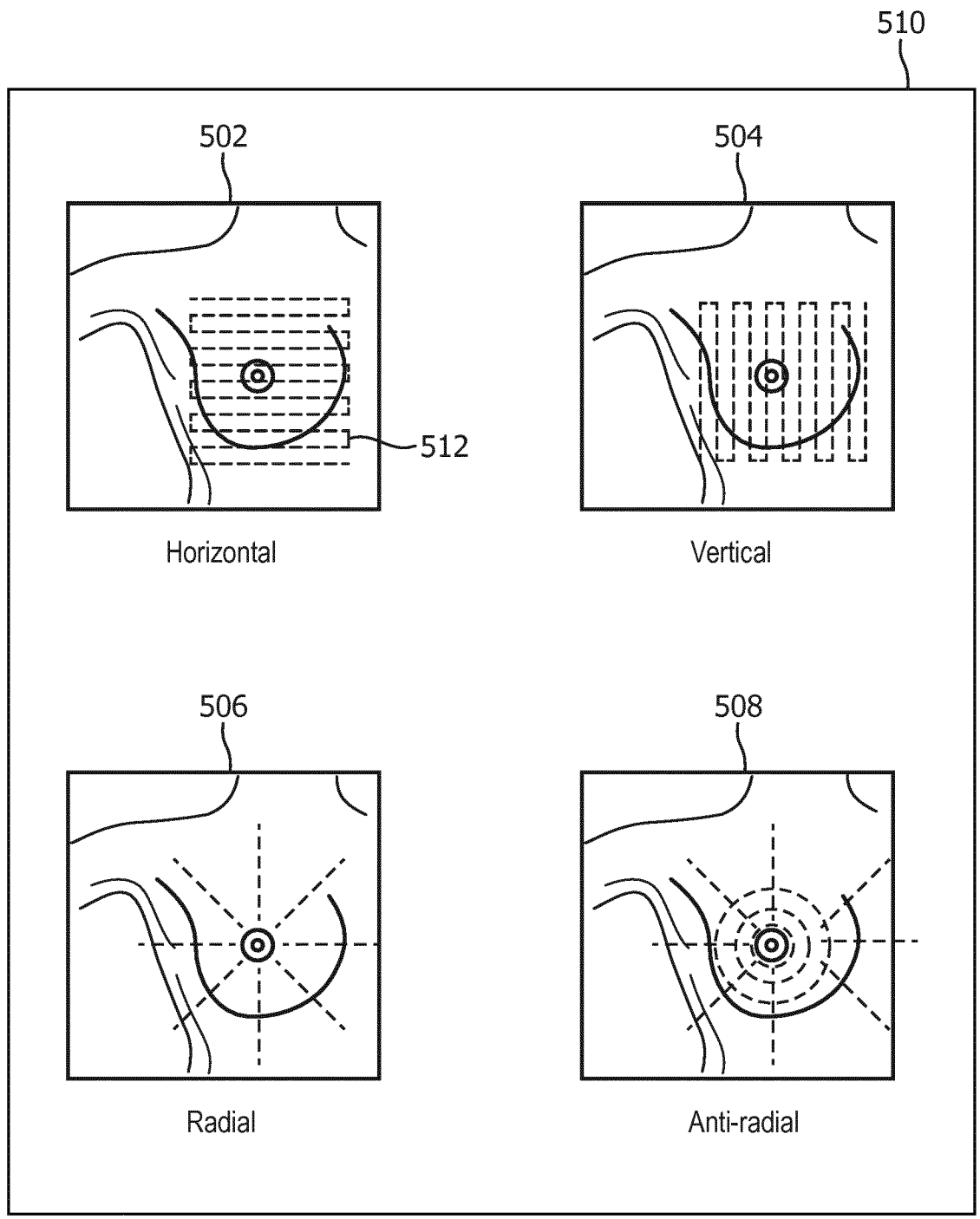
FIG. 5 shows exemplary scan patterns which may be provided for guidance to a user in accordance with further examples of the present disclosure, e.g., on user interface elements.

FIG. 5 illustrates exemplary scan patterns 502, 504, 506, and 508, which may be provided, e.g., as user interface elements on a user interface of an ultrasound system, for guidance to a user in accordance with further examples of the present disclosure. When implemented as user interface elements, the scan patterns 502, 504, 506, and 508 may interchangeably be referred to as UI elements 502, 504, 506, and 508 or scan pattern icons 502, 504, 506, and 508 of a user interface 510. One or more of the elements of user interface 510 may be used to implement one or more UI elements of other user interfaces described herein, for example the second user interface element 304 of FIG. 3 or the scan pattern icon 614 of FIG. 6. FIG. 5 shows a first scan pattern icon 502, a second scan pattern icon 504, a third scan pattern icon 506, and a fourth scan pattern icon 508, each providing a visual representation of a scan pattern for scanning breast tissue. The graphic in each of the illustrated examples shows a right breast, however it will be understood that a graphic showing a left breast graphic may be displayed for scanning the left breast of a subject.

In some examples, the user interface may be configured to display, during scanning, two scan patterns in sequence. For example, a first scan pattern may be displayed initially, and after image data has been acquired in in accordance with the first scan pattern, the user interface may replace the first scan pattern with a second scan pattern (e.g., an orthogonal scan pattern). In this manner, orthogonal views for the desired scan area may be obtained.

The first and second scan pattern icons 502 and 504, respectively, display a pair of orthogonally arranged raster patterns, which may be used in combination to obtain orthogonal views of breast tissue. In accordance with the horizontal raster pattern, the user may be instructed to scan the breast by sweeping the probe along generally parallel horizontal paths. After the full breast has been scanned in the horizontal direction, the user interface 510 may display the second scan pattern icon 504, which may instruct the user to scan the breast by sweeping the probe along generally parallel vertical paths. For any of the illustrated examples in FIG. 5, the user may place the probe generally perpendicularly to the scan path line (e.g., scan path line 512) and sweep the probe along the surface of the breast following probe the line. At the end of each horizontal or vertical line, the operator may slide the probe to the next horizontal or vertical line and continue sweeping the probe.

The scan path lines of the horizontal and/or vertical raster patterns may be continuous, e.g., the user may be instructed to sweep the probe along the surface of the breast without lifting the probe between adjacent parallel lines. In other examples, a different raster pattern may be used, such as one including a plurality of spaced disconnected parallel lines, in which case the user may be instructed to sweep the probe along each line (either from left to right, right to left, or from either direction) with optionally lifting the probe between each sweep. It will be appreciated that a variety of other scan pattern types may be used, for example using a pair of diagonal raster patterns arranged orthogonally to one another, the term raster implying that the scan path lines are generally parallel, or using a combination of radial and anti-radial scan path lines as described further below.

Alternatively or additionally, the user may be instructed to scan along and then perpendicularly to the direction of the lobes and ducts of the breast tissue. To that end, the user interface 510 may include a third scan pattern icon 506 and a fourth scan pattern icon 508 which display radial and anti-radial scan path lines. The radial scan pattern may include a plurality of radial scan path lines extending in a generally straight line from the nipple towards a perimeter of the breast as may be defined by the scan area boundary. The anti-radial scan pattern may include a plurality of scan path lines defined by concentric circles around nipple. In other examples, the anti-radial scan pattern may include a scan path line in the form of a single continuous spiral. The radial and anti-radial scan patterns may be used together in combination and/or in combination with one or more raster patterns to obtain orthogonal views of the breast tissue. That is, in some examples, the user may be instructed to scan the breast using the horizontal and the vertical raster patterns only. In other examples, the user may be instructed to scan the breast using the horizontal and the vertical raster pattern, which may be followed or preceded by instructions to scan the breast using the radial and anti-radial patterns.

The specific scan patters in FIG. 5 are provided for illustration only and it will be understood that other scan patterns, including patterns having different number and spacing or arrangement of lines, may be used. As described, the scan pattern may be based on any number of parameters, including the scan area (which may be an area covering the whole breast or a focus area), probe type, and/or desired view plane overlap, one or more of which may determine the appropriate scan pattern(s).

Figure 6:
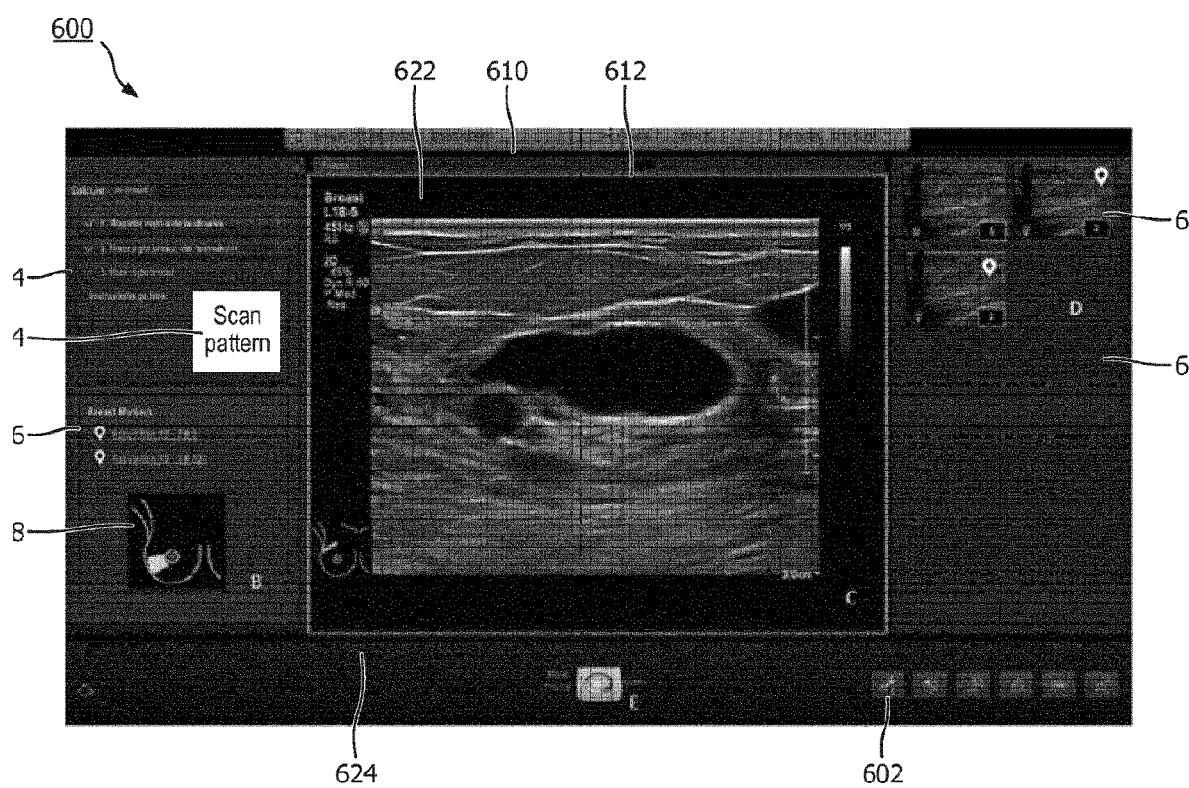
FIG. 6 shows a display screen of a user interface in accordance with some examples of the present disclosure.

FIG. 6 illustrates several user interface (UI) elements of user interface 600. One or more of the UI elements of user interface 600 may be used to implement one or more of the UI elements of other user interfaces described herein, such as user interface 300. Elements of user interface 600 may be provided in a display screen 602, a screen shot of which is shown in FIG. 6, and which may be displayed on a display (e.g., display 206) of an ultrasound system. FIG. 6 shows guidance UI element 604, markers UI element 606, feedback icon 608, main image area 610, image 612, scan pattern icon 614, stored images area 616, thumbnails 618, tracking status indicator 622, and body mark icon 624. The components shown in FIG. 6 are merely illustrative and other variations, including eliminating components, combining components, rearranging components, and substituting components are all contemplated.

The user interface 600 includes a guidance UI element 604. The guidance UI element 604 may be configured to display a scan pattern for guiding an operator during a breast scan. The guidance UI element 604 may include a scan pattern icon 614 which may include a visual representation of the scan pattern. The scan pattern icon 614 may be dynamic in that it may update automatically responsive to a detected change in position of the probe. As described, the position of the probe may be detected using the position tracking system and the detected position may be indicated via the scan pattern icon 614, for example by periodically illuminating (e.g., blinking) a pixel or group of pixels of the scan pattern. When a change in the position of the probe is detected, a pixel or group of pixels corresponding to the new position of the scan pattern may be periodically illuminated. In some examples, the position of the probe may be indicated by a cursor, the position of which may be dynamically updated based on the position of the probe. In some examples, the progress of the probe along the scan pattern may be indicated by illuminating a completed portion of the scan pattern while the portion yet to be scanned is not illuminated. As the probe advances along the scan pattern, more of the scan pattern is illuminated thus indicating the change in position and progress of the scan. In yet further examples, the scan pattern may initially be fully illuminated and as the probe progresses along the scan path, only portions yet to be scanned remain illuminated with completed portions being darkened as they are completed.

The scan pattern icon 614 may also be updated if a deviation from the scan pattern greater than a threshold deviation is detected. As the user scans the breast tissue, the position tracking system tracks the movement of the probe relative to the breast. The system may calculate an amount of deviation (e.g., a percent or standard deviation) from the expected path and compare the deviation to a threshold value. Small amounts of deviation may be tolerable and may not require adjustment. However, if a deviation exceeds a threshold amount, such as may cause insufficient overlap of image data, the system may re-calculate the scan pattern and update the scan pattern icon 614 to display the re-calculated scan pattern. Thus, even if the user fails to adhere to the expected path, the system may provide dynamic guidance to allow the user to make adjustments during the scanning process, which may increase the likelihood that sufficient image data is acquired of the full breast tissue.

The user interface 600 may include a markers UI element 606. The markers UI element 606 may include a feedback icon 608. The feedback icon 608 may include a graphic of the organ being scanned, in this example a breast graphic, overlaid with a filled region (e.g., a colored region) corresponding to the already scanned area. The feedback icon 608 may be dynamic in that it may be automatically updated as more of the breast is scanned. In this manner, the user can visualize in real time how much of the breast has already been scanned, and how much breast area remains to be scanned. When all scan path lines in one direction have been swept and image data has been acquired in one direction (e.g., horizontal direction, or radial direction), the filled region overlay of the feedback icon 608 is cleared in preparation for scanning in the orthogonal direction. As the user scans in the orthogonal direction, the feedback icon 608 is dynamically overlaid with a filled region corresponding to the scanned area in the orthogonal direction.

The user interface 600 may include a main image area 610. The main image area 610 may display an image 612, which may be a B-mode image generated from acquired image data. The image 612 may be a live image, which may be displayed in real time as the image data is being acquired. A listing or thumbnails of stored single or multi-frame image files may be provided in a stored images area 616. In the illustrated example, the stored images area 616 display a plurality of thumbnails 618, each of which is associated with a single or a multi-frame image. The user may click on any of the thumbnails 618 to display the frames of that image. If a thumbnail is selected, live mode is paused and the main image area 610 is used to display the image frames of the selected thumbnail. In some examples, a thumbnail may include a bookmark indicator, which may indicate the presence of bookmarked frames in the image file. A listing of the bookmarks may also be provided in the markers UI element 606, which may enable the user to quickly navigate to a particular bookmarked frame. Selecting a bookmark from the listing may cause the respective bookmarked image frame to be displayed in the main image area 610.

In some examples, the user interface 600 may include a body mark icon 624. The body mark icon 624 may be provided in the main image area 610, for example adjacent to the live image. In some examples, the body mark icon 624 may be provided adjacent to the side of the image corresponding to the breast side being scanned. The body mark icon 624 may include a probe location marker overlaid on a visual representation of the organ being scanned, in this example on a breast graphic. In some examples, the probe location marker may have a size and/or orientation relative to the breast graphic that estimates the footprint and orientation of the probe with respect to the breast.

The user interface 600 may include a tracking status indicator 622 which may provide an indication of the status or quality of position tracking. In some examples, the tracking status indicator 622 may be provided in the form of a colored frame around the displayed image 612. The color of the frame may indicate if there are issues with the position tracking. For example, the color of the frame may be green when probe position is properly tracked. The color of the frame may change to red if the probe falls outside of the tracking field or if interference is affecting the quality of the position tracking. In some examples, different degrees of reduced tracking quality may be indicated using a color scale of different colors (e.g., green for good quality, orange for reduced quality, and red when no tracking data is being received). In other examples, the tracking status indicator 622 may be provided using a different indicator, such as a traffic light graphic, a color bar, or another type of graphic or an alphanumeric indicator.

Figure 7:
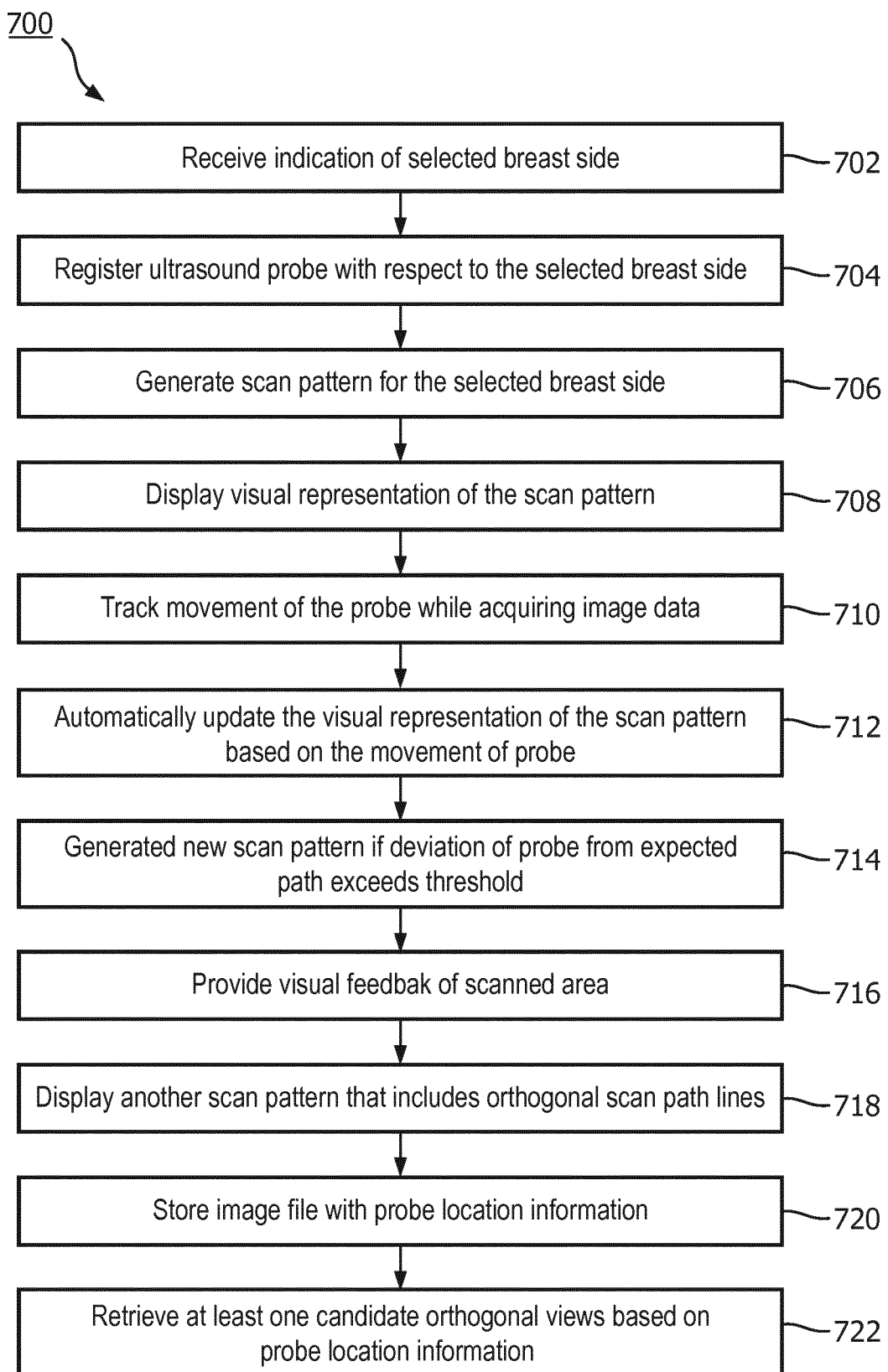
FIG. 7 shows a flow diagram of a process which may be performed with ultrasound systems in accordance with the present disclosure.

FIG. 7 shows a flow diagram of a process 700. The process 700 may utilize one or more aspects of the present disclosure, such as one or more elements of user interfaces in accordance with the examples herein. FIG. 7 shows blocks 702, 704, 706, 708, 710, 712, 714, 716, 718, 720, and 722. The blocks shown in FIG. 7 are merely illustrative, and other variations, including eliminating, combining, rearranging, and substituting blocks are all contemplated.

As shown in block 702, the process may begin by receiving an indication of a selected breast side. The indication may be received responsive to user input via the user interface. For example, the user interface may be configured to display icons which may enable the user to select either the left or right breast side. Any of the user inputs described may alternatively be provided via text input, such as via hard or soft keyboard of the user inter interface. Responsive to the indication of selected breast side, the processor may determine if probe spatial registration information has been generated for the selected breast side. If yes, the processor may enter scanning mode and cause the user interface to display a live image on a display (e.g., display 206).

If probe spatial registration information is not available for the selected breast side, a probe registration process may be initiated, during which the probe may be registered with respect to the selected breast side, as shown in block 704. For example, registering the probe with respect to the selected breast side may include providing instructions, via the user interface, for placing the ultrasound probe at a plurality of anatomical landmarks of the selected breast side, detecting a spatial location of the probe at each of the plurality of anatomical landmarks, and storing the spatial location of the probe at each of the plurality of anatomical landmarks as the probe spatial registration information. In some examples, the step of providing instruction may include displaying a plurality of registration icons, each including a visual representation of the selected breast side overlaid with a probe placement marker at one of the plurality of anatomical landmarks. In some examples, one or more of the registration icons may be displayed concurrently or in sequence.

The processor may generate a scan pattern for the selected breast side (as shown in block 704) and cause the user interface to display a visual representation of the scan pattern (as shown in block 706). The scan pattern may be generated in accordance with any of the examples described herein. The visual representation of the scan pattern may include a graphic corresponding to the tissue or organ that is being scanned (e.g., a breast graphic) which is overlaid with the scan pattern. As shown in block 710, the processor may be configured to track the movement of the probe while image data is being acquired, for example using probe position data received from a position tracking system.

As shown in block 712, the visual representation of the scan pattern may be automatically updated based on the movement of the probe. For example, the user interface may be configured to provide an indication of current position of the probe, such as in the form of a cursor or illuminating a portion of the scan pattern differently to indicate progress of the probe relative to the scan pattern. The user interface may be configured to dynamically update the indication of probe position based on the tracked movement of the probe. In some examples, the user interface may be configured to generate a new scan pattern if a deviation of the probe from the expected path exceeds a threshold, as shown in block 714. For example, the user interface may be configured to enable a user to specify a minimum view plane overlap. The processor may receive the indication of minimum view plane overlap and generate the scan pattern (e.g., the initial scan pattern(s)) to provide the desired minimum overlap. The system may then track movement of the probe, using the spatial location information, and determine deviation from the initial scan pattern. The deviation may be compared to a threshold amount which has been selected to ensure that acquired images overlap by at least the desired amount. If the movement of the probe indicates otherwise, a new scan pattern may be generated and displayed.

As shown in block 716, the user interface may provide visual feedback of the scanned area, for example by displaying an icon of a breast graphic overlaid with a demarcated region that corresponds to the estimated scanned area. The region may be colored (e.g., green to indicate "completed"), or filled with a cross hatch or shading. In some examples, the remaining area to be scanned may instead be demarcated for example using a color (e.g., orange) to indicated that this area is yet to be completed.

As shown in block 718, the user interface may display multiple scan patterns in sequence, for example a first scan pattern and a second scan pattern that includes orthogonal scan path lines, as previously described. In each instance, the user interface may dynamically update the visual representation of the scan pattern to indicate progress and/or compliance with the scan pattern.

Acquired image data may be stored in memory (e.g., memory 134) along with the probe location information. For example, the image data may be stored in a standardized image file (e.g., single or multi-frame DICOM image file), which is appended with metadata corresponding to the probe position (e.g., x, y, and z coordinates and orientation of the probe) during acquisition of each frame in the image file. This may enable efficient and simplified retrieval of relevant image frames at a later time, as shown in block 722 and described further below with reference to FIGS. 8-10.

Figure 8:
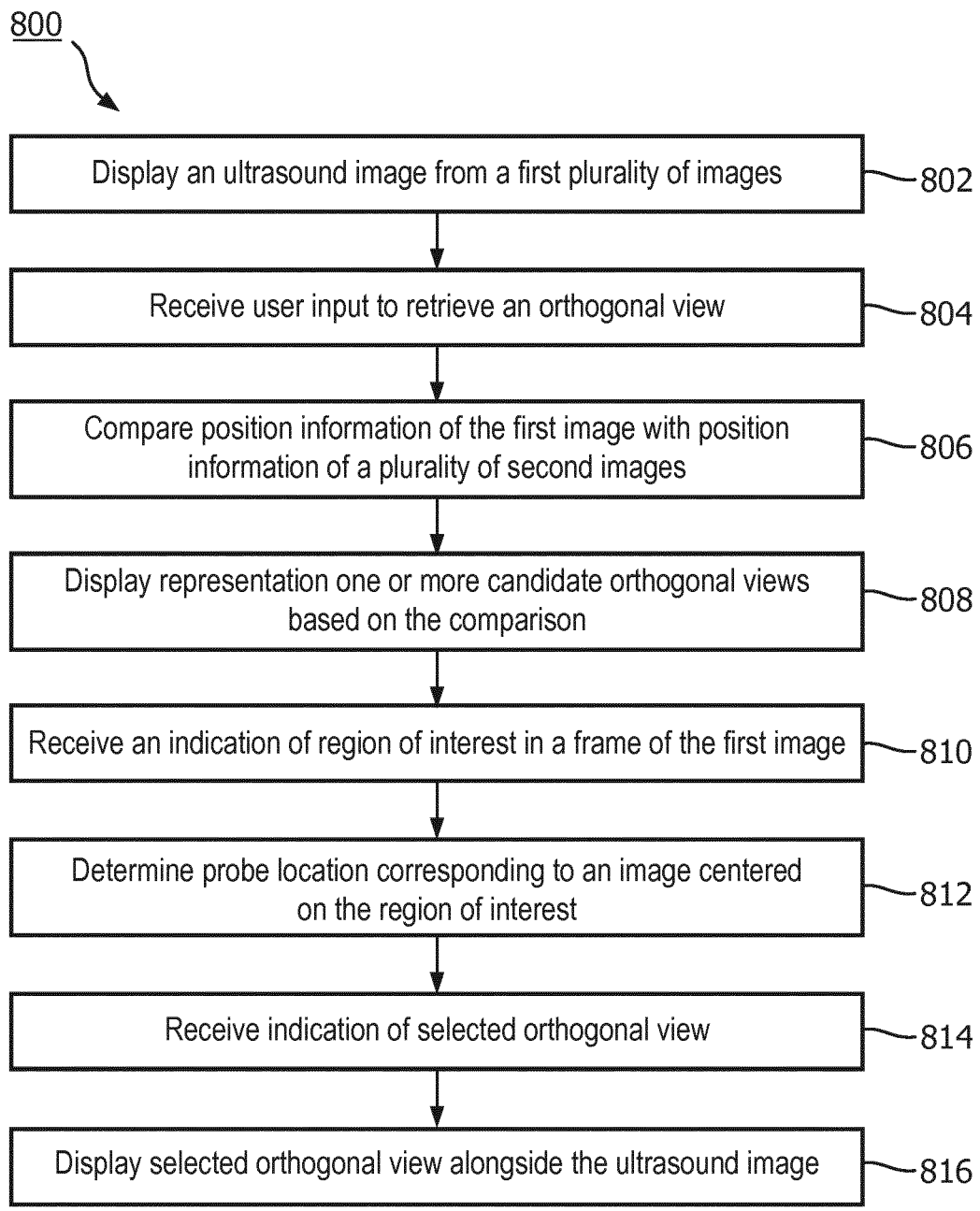
FIG. 8 shows a flow diagram of another process which may be performed in accordance with the present disclosure.
Figure 9:
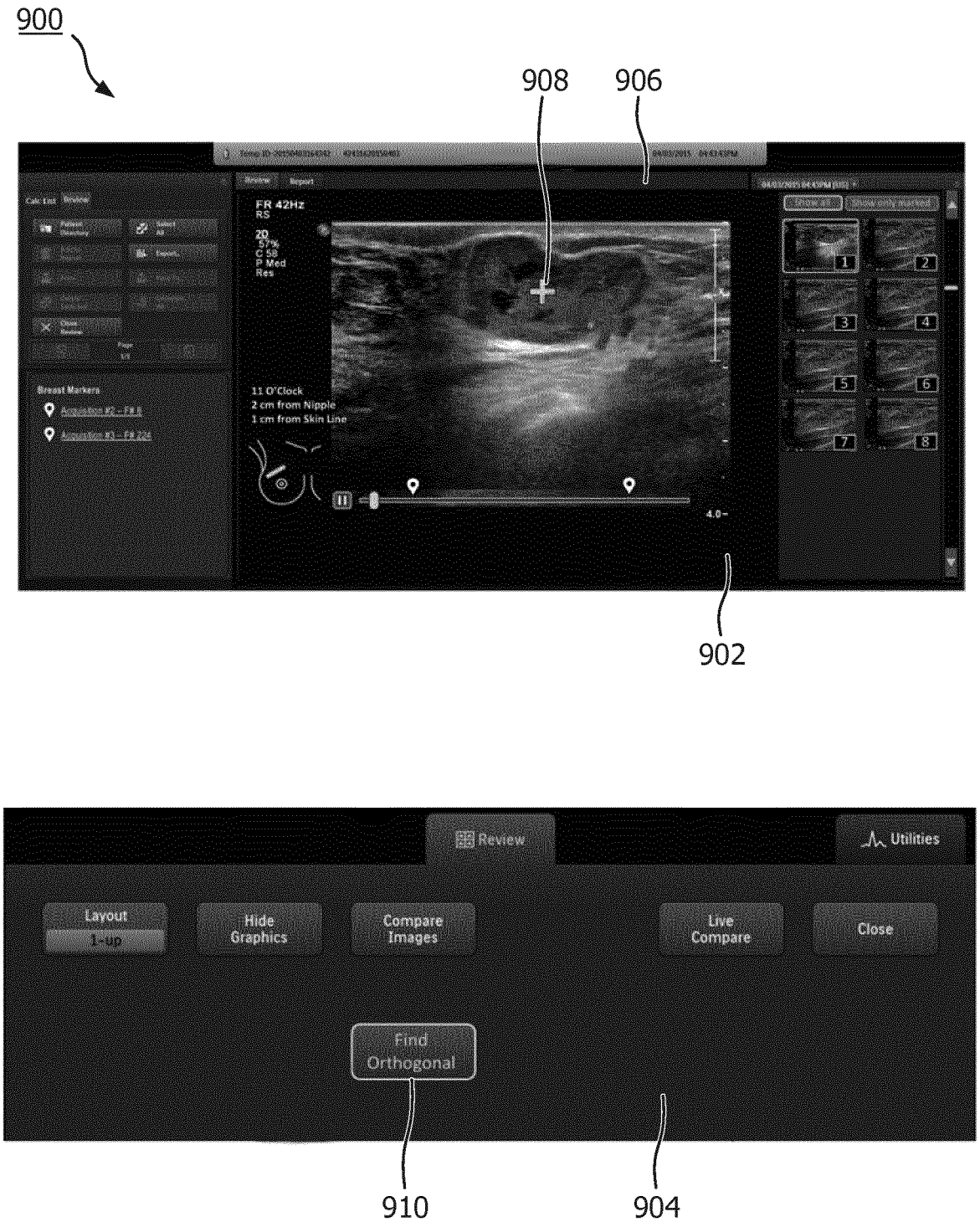
FIG. 9 shows user interface elements in accordance with further examples of the present disclosure.
Figure 10:
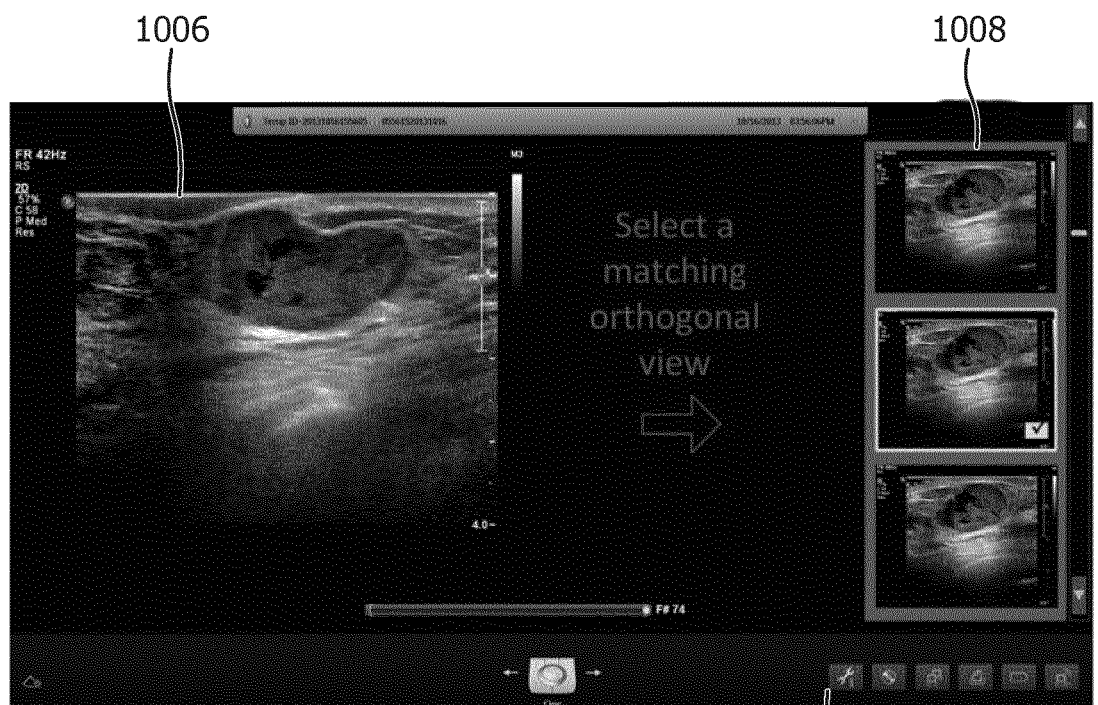
FIG. 10 shows display screens of user interfaces in accordance with further examples of the present disclosure.
Figure 10:
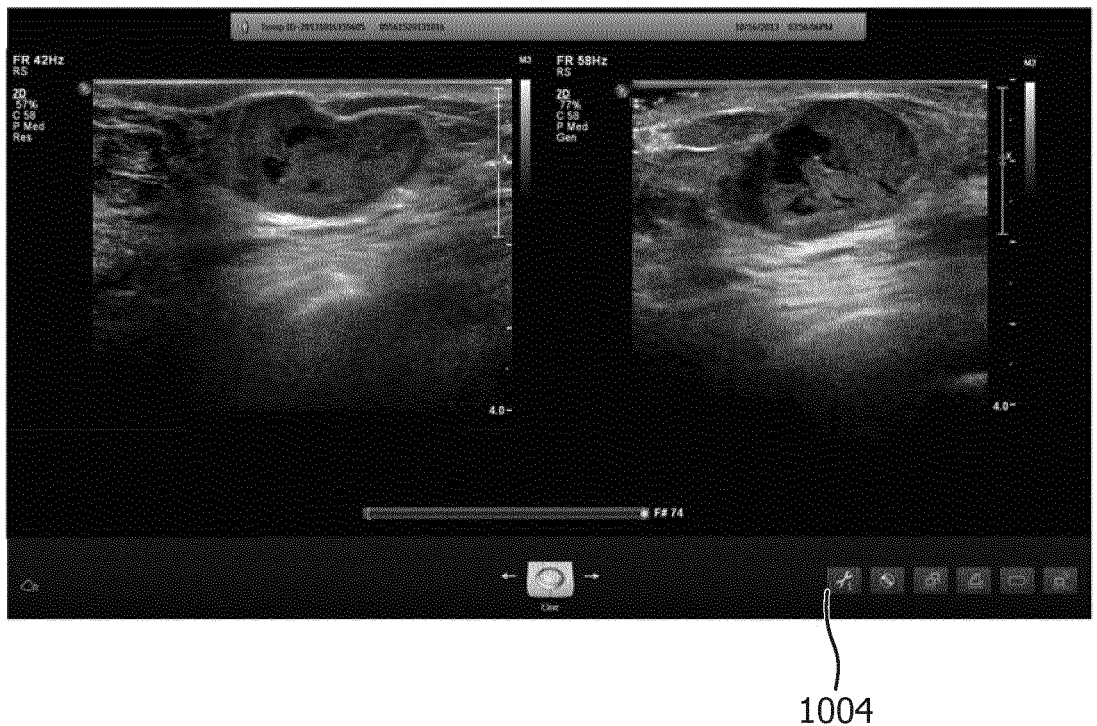

FIG. 8 shows a flow diagram of another process in accordance with the present disclosure. The process 800 may utilize aspects of the present disclosure such as one or more elements of user interfaces described herein. FIGS. 9 and 10 show examples of user interface elements that may apply to the process 800. FIG. 9 shows display screens 902 and 904 of user interface 900. The display screen 902 may be provided for example on display 206 of ultrasound imaging system 200. Similar to display screen 602, the display screen 902 may be configured to display an ultrasound image 906, which may be a stored image. In some examples, the image 906 may be bookmarked image frame. The image 906 may include a region of interest (ROI), which may be a breast lesion. The display screen 904 may be provided on a touch-sensitive display, such as touch screen 218 of the ultrasound imaging system 200. The display screens 902 and 904 may enable the user to make relevant measurements of the ROI, efficiently retrieve orthogonal views, and document the lesion, for example for inclusion in a report. FIG. 10 shows display screens 1002 and 1004 of a user interface in accordance with further examples herein. The display screen 1002, which may be provide on display 206 of the ultrasound imaging system 200, includes a first image frame 1006 of the left hand side of the screen and candidate orthogonal views 1008 on the right hand side of the screen. The arrangement of the images on the screen may be changed, for example displaying the orthogonal views in a different location such as on the left hand side or in the lower portion of the screen 1002. The display screen 1004 shows the first image 1006 and the selected orthogonal view (e.g., in this example, the second image from the candidates 1008) in a side by side arrangement. The elements shown in FIGS. 8-10 are merely illustrative and other variations, including eliminating, combining, rearranging, and substituting elements are all contemplated.

The process 800 may start with displaying an ultrasound image from a first plurality of images, as shown in block 802. Each of the images in the first plurality may be associated with probe position information (e.g., spatial location of the probe during acquisition of the image) and stored with their corresponding position information. In some examples, the process may include the step of arranging the images of the first plurality in spatially sequential prior to displaying the first image on the screen. This step may occur automatically when a user invokes a review workflow. Alternatively, this step may occur during image data acquisition, such as at the end of a scanning workflow. As shown in block 804, the user interface may be configured to receive user input to retrieve an orthogonal view. For example, the user interface may be configured to provide a soft control, such as orthogonal view button 910 in FIG. 9, or other user control for example on an analysis workstation. The user may operate the soft control and a processor may, responsively, automatically identify candidate orthogonal views.

To that end, the processor may compare position information of a displayed image frame with position information of a plurality of second images, as shown in block 806. The plurality of second images may be images acquired by following an orthogonal sweep protocol. For example, the displayed image may be selected from scanning in a side-to-side orientation, and the plurality of second images would then be selected from the images acquired while scanning in an up/down orientation or vice versa. The processor may be configured to identify one or more candidate orthogonal views by identifying those images that are associated with position information closest to the position information of the displayed image frame. In some examples, the position information may include x, y, and z coordinates of the probe (or coordinates in another frame of reference) and/or probe orientation. As described, in some examples, the images acquired through sweeps in one direction (e.g., with the probe oriented one way) may be stored in a separate set from images acquired through sweeps in another direction (e.g., with the probe oriented at an angle from the first orientation, which angle may be approximately 90 degrees). In some examples, the processor may be able to determine the relative angle between the image planes (also revered to as view planes). When probe orientation information is available, the images need not be stored in separate (e.g., orthogonal) sets and the processor may be configured to automatically sort the images into sets prior to the orthogonal view retrieval step or the processor may directly retrieve orthogonal candidates from the single set based on the probe orientation.

The processor may be configured to cause the user interface to display representations of the one or more candidate orthogonal views that were identified based on the comparison, as shown in block 808. In some examples, displaying representations of the one or more candidate orthogonal views may include displaying thumbnails or a reduced quality image (e.g., a smaller resolution and/or a smaller size image) of each of the images corresponding to the identified orthogonal view candidates, e.g., as in the display screen 1002 in FIG. 10. In some examples, the orthogonal candidates may be displayed on the same display screen, as shown in FIG. 10. The user interface may be configured to receive a selection of one of the candidate orthogonal views (e.g., by clicking on or selecting a checkbox next to one of the representations), as shown in block 814. The user interface may then display the selected one of the candidate orthogonal views (see block 816) as a second image frame in a side by side arrangement with the first image frame, e.g., as in the display screen 1004 in FIG. 10.

In some examples, the processor may be configured to select the orthogonal view candidates using an adjusted probe location. For example, the displayed image frame may include a region of interest (ROI), which may not be centered within the image frame. The user may select the ROI, such as by placing a cursor 908 within the ROI and typically near the center of the ROI. The processor, responsive to receiving the indication of the ROI (see block 810), determines a probe spatial location corresponding to an image centered on the region of interest (see block 812), such as by calculating an offset distance and adjusting the probe position information by the offset distance. The processor may then set the first position information as the probe spatial location corresponding to an image centered on the region of interest, and retrieve orthogonal view candidates using the adjusted probe location. As previously described, the candidates are displayed and the user may select the appropriate orthogonal view from the candidates. Upon identification of the appropriate orthogonal views, relevant measurements may be obtained, for example for inclusion with the images in a report. Typically, the width of the ROI, which may be a suspicious lesion, is measured in both of the orthogonal views. The two orthogonal widths of the ROI may be used by the processor to automatically identify a subset of images that intersect the ROI. This subset may be sufficient to fully document the ROI (e.g., suspicious lesion) and the remaining acquired images need not be retained and/or exported for later review.

The process 800 and elements of the user interfaces 900 and 1000, examples of which are shown in FIGS. 9 and 10, may be implemented on an ultrasound imaging system, such as the ultrasound imaging system 100. Such ultrasound imaging system may include, for example, a user interface, a processor configured to control operations of the user interface, and a memory, which may be local memory or a remote storage device such as a PACS server. The memory may store image files (e.g., DICOM files) that include position data. The user interface of the ultrasound imaging system may be configured to enable a user to automatically retrieve orthogonal view candidates based on the position data. In some examples, the ultrasound imaging system may also include or be configured for coupling to a probe with position tracking and the ultrasound imaging system may include functionality for recording the position tracked images.

It will be understood that any one of the examples, embodiments or processes described herein may be combined with one or more other examples, embodiments and/or processes or be separated and/or performed amongst separate devices or device portions in accordance with the present systems, devices and methods. Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
   a user interface comprising a display;
   a processor communicatively coupled to the user interface and configured to be communicatively coupled to a probe; and
   a memory communicatively coupled to the processor and comprising processor-executable instructions for displaying ultrasound images, the processor-executable instructions including instructions to:
      display a first image frame of one of a first plurality of ultrasound images on the display, wherein each of the first plurality of ultrasound images is stored with corresponding probe position information, wherein the first image frame is associated with a first position information, and wherein the probe position information corresponds to a spatial location of the probe with respect to a subject;
      receive user input to retrieve an orthogonal view;
      compare the first position information with position information stored with a second plurality of ultrasound images to identify one or more image frames in the second plurality of ultrasound images that are associated with position information closest to being orthogonal to the first position information; and
      display a representation of each of the one or more image frames as candidate orthogonal views.

2. The ultrasound imaging system of claim 1, wherein the instructions to display a representation of each of the one or more image frames as candidate orthogonal views include instructions to display a reduced quality image of each of the one or more image frames.

3. The ultrasound imaging system of claim 1, wherein the memory further comprises instructions to arrange the first plurality of image files in spatially sequential order prior to displaying the first image frame.

4. The ultrasound imaging system of claim 1, wherein the memory further comprises instructions to:
   receive an indication of a region of interest;
   determine a probe spatial location corresponding to an image centered on the region of interest; and
   set the first position information as the probe spatial location corresponding to an image centered on the region of interest.

5. The ultrasound imaging system of claim 1, wherein the memory further comprises instructions to enable the user interface to receive a selection of one of the candidate orthogonal views and display the selected one of the candidate orthogonal views as a second image frame in a side by side arrangement with the first image frame.

6. The ultrasound imaging system of claim 5, wherein the memory further comprises instructions to:
   receive an indication of first and second widths of a region of interest in the first and second image frames, respectively;
   determine a first subset of images from the second plurality of images that intersect the view plane of the first image frame only within a region defined by the first width;
   determine a second subset of images from the first plurality of images that intersect the view plane of the second image frame only within a region defined by the second width; and
   delete one or more images from the first and second pluralities of images that are not included in the first and the second subsets.

7. The ultrasound imaging system of claim 1, wherein the processor is further configured to associate individual frames of an acquired ultrasound image with position information corresponding to a position of the probe during acquisition of a respective frame and store the ultrasound image with the associated position information in memory.

8. The ultrasound imaging system of claim 1, further comprising a probe configured to be operatively associated with a position tracking system and wherein the processor is further configured to register one or more anatomical landmarks of the subject in relation to the position tracking system.

9. The ultrasound imaging system of claim 8, wherein the processor is configured to cause images acquired with the probe in a first orientation to be stored as the first plurality of ultrasound images and images acquired with the probe at an angled orientation to be stored as the second plurality of ultrasound images.

10. A non-transitory computer-readable medium comprising processor-executable instructions for displaying ultrasound images, the processor-executable instructions comprising instructions to:
    display a first image frame of one of a first plurality of ultrasound images, wherein each of the first plurality of ultrasound images is stored with corresponding probe position information, wherein the first image frame of the ultrasound image is associated with a first position information, and wherein the probe position information corresponds to a spatial location of the probe with respect to a subject;
    receive user input to retrieve an orthogonal view;
    compare the first position information with position information stored with a second plurality of ultrasound images to identify one or more image frames in the second plurality of ultrasound images that are associated with position information closest to being orthogonal to the first position information; and
    display a representation of each of the one or more image frames as candidate orthogonal views.

11. The non-transitory computer-readable medium of claim 10, further comprising instructions to arrange the first plurality of image files in spatially sequential order prior to displaying the first image frame.

12. The non-transitory computer-readable medium of claim 10, further comprising instructions to:
    receive an indication of a region of interest;
    determine a probe spatial location corresponding to an image centered on the region of interest; and set the first position information as the probe spatial location corresponding to an image centered on the region of interest.

13. The non-transitory computer-readable medium of claim 10, further comprising instructions to:
receive an indication of first and second widths of a region of interest in the first and second image frames, respectively;
determine a first subset of images from the second plurality of images that intersect a view plane of the first image frame only within a region defined by the first width;
determine a second subset of images from the first plurality of images that intersect a view plane of the second image frame only within a region defined by the second width; and
delete one or more images from the first and second pluralities that are not included in the first and the second subsets.

* * * * *